United States Patent [19]

Bhat

[11] Patent Number: 5,767,270

[45] Date of Patent: Jun. 16, 1998

[54] ACYLATION OF NUCLEOSIDES WITH N-ACYL TETRAZOLE

[75] Inventor: Balkrishen Bhat, Carlsbad, Calif.

[73] Assignee: ISIS Pharmaceuticals, Inc., Carlsbad, Calif.

[21] Appl. No.: 936,984

[22] Filed: Sep. 25, 1997

[51] Int. Cl.$^6$ .................. C07H 1/00; C07D 249/08
[52] U.S. Cl. .................................. 536/55.3; 548/253
[58] Field of Search ................... 536/55.3; 548/253

[56] References Cited

PUBLICATIONS

Stawinski et al. J.C.S. Chem. Comm. 1976, p. 243 ff.

*Primary Examiner*—Gary L. Kunz
*Attorney, Agent, or Firm*—Woodcock Washburn Kurtz Mackiewicz & Norris LLP

[57] ABSTRACT

Methods for selective acylation of nucleosides and nucleotides are provided. The methods can provide monoacylated products and are useful for forming N-acylated nucleosides, nucleotides, and dimers and oligomers thereof.

20 Claims, No Drawings

ACYLATION OF NUCLEOSIDES WITH N-ACYL TETRAZOLE

The present invention is directed to methods for selective acylation of nucleosides and nucleotides by reacting a nucleoside or nucleotide with an N-acyl tetrazole. The present invention provides methods for monoacylation, such as monobenzoylation, of exocyclic amine groups of nucleosides and nucleotides.

BACKGROUND OF THE INVENTION

Modified oligonucleotides are important for the development of new therapeutic agents and for research in areas such as selective inhibition of gene expression. Synthesis of modified oligonucleotides often requires the protection of certain sites of the oligonucleotides during modification. Typically, the protecting groups are subsequently removed, i.e. the protected sites are "deprotected".

The protection of exocyclic amino groups of nucleosides and nucleotides is of particular importance in the synthesis of modified oligonucleotides. Acyl protecting groups are particularly useful because they are relatively stable under mildly basic or acidic reaction conditions, but can be readily removed when synthesis is completed. One method for protection of exocyclic amino groups using acyl protecting groups consists of peracylation, followed by selective deacylation, of hydroxyl groups with a base to obtain the desired N-acylated nucleosides. Schaller et al., *J. Am. Chem. Soc.* 1963, 85, 111. More recently, a preferred procedure has been "transient protection". One method of transient protection requires temporary masking of hydroxyl groups as trimethylsilyl ethers, followed by reaction with excess benzoyl chloride or isobutyric anhydride in pyridine. Subsequent treatment with base provides N-acylated nucleosides. Ti et al., *J Am. Chem. Soc.* 1982, 104, 1316. However, the formation of undesirable side products has been reported with this method of transient protection. Another method of transient protection, described in Sinha et al., *Tetrahedron Lett.* 1995, 36, 9277, uses protection of sugar hydroxyl groups by silylation. Absolutely dry reaction conditions and fresh preparation of acylating reagent, as well as subsequent removal of silyl groups, are required.

Benzoylation has been used for the protection of hydroxy and amino functional groups in nucleosides and nucleotides. Reactants used for benzoylation include benzoyl chloride-pyridine, benzoic anhydride, benzoyl cyanide, and benzoylimidazole. A solution of benzoyl chloride in dioxane, in admixture with tetrazole and triethylamine, has been used for benzoylation of nucleosides. Stawinski et al., *J.C.S. Chem. Comm.*, 1976,243. The solution was maintained at room temperature for 15 minutes and filtered; the filtrate was used as the benzoylating reagent. However, the procedure generally resulted in the introduction of more than one benzoyl group to the nucleoside, or in a mixture of products. Furthermore, the component of the filtrate which was responsible for the benzoylation was neither identified nor isolated. Thus, it is unlikely that such a method can be readily controlled or used for selective acylation.

Accordingly, there remains a need for methods for controlled protection of groups, particularly exocyclic amino groups, of nucleosides and nucleotides during synthetic procedures. In particular, monoacylation and ease of deprotection are desirable. The present invention is directed to these, as well as other, important ends.

SUMMARY OF THE INVENTION

The present invention provides methods for selectively acylating an exocyclic amino group of a nucleoside or a nucleotide. Oligomeric nucleosides and nucleotides can also be selectively acylated by the method of the present invention. The method includes reacting the nucleoside or nucleotide with an N-acyl tetrazole. In preferred embodiments, the N-acyl tetrazole is N-benzoyl tetrazole.

The present invention also provides methods for preparation of, N-acylated nucleosides or nucleotides, by reacting the nucleosides or nucleotides with an N-acyl tetrazole, such as N-benzoyl tetrazole. The methods can further include subsequent deacylation of the N-acylated nucleoside or nucleotide, and is amenable to automation.

The present invention further provides substantially pure, crystalline N-benzoyltetrazole.

It has been surprisingly found that the acylation of a nucleoside or nucleotide can be controlled so that only the exocyclic amino group is acylated. The acylation is accomplished by the use of an N-acyl tetrazole. Preferably, the N-acyl tetrazole is N-benzoyl tetrazole.

The methods of the present invention can be used to selectively N-acylate nucleosides or nucleotides having an exocyclic amine group. By "selective" is meant that a single acyl group can be introduced to a nucleoside or nucleotide at the exocyclic amine group, leading to improvements in synthesis involving such molecules.

The methods of the present invention are amenable to automation, and can be carried out on a solid support such as, for example, controlled pore glass.

While it is not intended that the present invention be bound by any particular theory or theories, it is believed that the selectivity provided by the methods of the present invention is due, in part, to the purity of the N-acyl tetrazole used therein. It is believed that the use, according to the method of the present invention, of a substantially pure, crystalline N-acyl tetrazole, minimizes or eliminates the production of undesired side products. As reported by Stawinski, supra, the use of a filtrate containing unidentified and unpurified reagents can yield unpredictable reaction products and significant amounts of diacylation.

Suitable N-acyl tetrazoles for use in the method of the present invention include N-benzoyl tetrazole, p-toluyllthionocarbonyl tetrazole, N-benzoyloxohydroxybenzotriazole, isobutyryl tetrazole and other N-acyl moieties. N-benzoyl tetrazole and phenyl-substituted counterparts thereof are particularly preferred.

In contrast to known methods for N-acylation of nucleotides and nucleosides, the method of the present invention allow for control and selectivity. The method uses a substantially pure N-acyl tetrazole such as, for example, N-benzoyltetrazole. By "substantially pure" is meant a reagent comprising at least about 90%, preferably at least about 95%, and more preferably at least about 99%, of the desired N-acyl tetrazole. Thus, the methods preferably use a N-acyl tetrazole in purified, crystalline form. The N-acyl tetrazole can be recrystallized according to methods well known to those skilled in the art. Suitable solvents for crystallization will depend upon the particular N-acyl tetrazole to be used. For example, N-benzoyl tetrazole can be readily recrystallized from hexanes as colorless needles.

N-acyl tetrazoles can be synthesized by contacting an acyl halide with 1-H-tetrazole in the presence of a base. For example, reaction of benzoyl chloride with 1-H-tetrazole in the presence of triethylamine readily produces N-benzoyl chloride, which can then be recrystallized (Hayakawa, Y., *J. Am. Chem. Soc.*, 1990, 112, 1691).

The substantially pure, crystalline N-acyl tetrazole can be dissolved in a small amount of solvent, such as, for example, the minimum amount of a suitable solvent which will form a clear solution of the crystalline N-acyl tetrazole at room temperature. "Room temperature", as used herein, refers to an ambient temperature from about 20° C. to about 30° C. Less preferably, crystalline N-acyl tetrazole can be dissolved in a solvent by gently heating, i.e. heating to a temperature from about 10° C. to about 30° C. above room temperature. The solution of crystalline N-acyl tetrazole can then be admixed with a solution of a nucleoside or nucleotide which is to be N-acylated. The particular solvent or solvents for a particular N-acyl tetrazole can be readily ascertained by one skilled in the art. For example, acetonitrile is a suitable solvent for N-benzoyl tetrazole.

Treatment of nucleosides and nucleotides with N-acyltetrazole according to the methods of the present invention can be carried out in any solvent which dissolves both the nucleoside or nucleotide, and the N-acyl tetrazole. Preferred solvents are polar, aprotic solvents. Examples of polar aprotic solvents suitable for use in the methods of the present invention include acetonitrile, tetrahydrofuran, dimethylformamide and DMSO. Preferably, the solvent is dried before use, using procedures known to those skilled in the art. The nucleoside or nucleotide to be protected is contacted with the N-acyl tetrazole, preferably with agitation such as, for example, stirring. The reaction components are generally heated to about 65° C. Typical reaction times are from about ¼ hour to about 2 hours, depending upon the composition of the nucleoside or nucleotide, and of the N-acyl tetrazole. For example, it has been observed that monobenzoylation of 3'-O-TBDPS-2'-O-methyl-5' formaldoxime adenosine was completed (with a yield of 75% with no dibenzoylation) within 75 minutes. Reaction progress can be monitored by removing aliquots after, for example, 1 hour and at regular intervals thereafter and analyzing the aliquots by thin layer chromatography on silica gel plates using methanol and dichloromethane or ethyl acetate, hexane and methanol as developing solvents.

The methods of the present invention can be used to N-acylate, and in particular monoacylate, any nucleoside or nucleotide having an exocyclic amine group. Nucleosides and nucleotides which can be N-acylated according to the methods of the present invention include purine nucleosides having an exocyclic amine group and pyrimidine nucleosides having an exocyclic amine group, and the respective nucleotides. Particular nucleosides and nucleotides suitable for N-acylation according to the methods of the present invention include, but are not limited to, cytidine, adenosine, guanidine, deoxyadenosine, deoxycytidine, deoxyguanosine, 5- cytidine, 2,6-diaminopurine, 7-deazaadenine, 7-deazaguanosine, 2'-O-methyladenosine, 2'-O-methyl-5-methylcytidine, and 2'-O-methoxyethylcytidine. As used herein, "alkyl" refers to a $C_1$-$C_8$ saturated hydrocarbon chain, which may be straight, branched, or cyclic. The 2-deoxy forms of the recited nucleosides and nucleotides are also suitable for use in the methods of the present invention. Oligomeric nucleosides and nucleotides having one or more exocyclic amine groups are also suitable for N-acylation according to the methods of the present invention.

Also suitable for N-acylation according to the methods of the present invention are various modified nucleosides, nucleotides, and dimers and oligomers thereof, either synthetic or naturally occurring. For example, the methods of the present invention can be used in N-acylation of nucleotides, nucleosides and oligomers thereof, having modified portions, such as, for example, modified sugars moieties, modified base moieties, or modified sugar linking moieties. Suitable nucleosides, nucleotides, and oligomers thereof are generally functionally interchangeable with naturally occurring analogous compounds but have one or more structural differences from the naturally occurring compounds. Exemplary among these are phosphorothioate, phosphoridithioate, methyl phosphonate, phosphotriester or phosphoramidate inter-nucleoside linkages in place of phosphodiester linkages; deaza or aza purines and pyrimidines; pyrimidine bases having substituent groups at the 5 or 6 position; purine bases having altered or replacement substituent groups at the 2, 6 or 8 positions; and sugars having substituent groups at the 2' position, substitutions for one or more of the hydrogen atoms of the sugar, or carbocyclic or acyclic sugar analogs. Suitable compounds are described in U.S. Pat. No. 5,359,051, the disclosure of which is hereby incorporated herein by reference in its entirety. Preparation of phosphorothioate, methylphosphonate, phosphodiester, phosphotriester or phosphoroamidate nucleosides, nucleotides and oligomers thereof is described in U.S. Pat. No. 5,212,295, the disclosure of which is hereby incorporated herein by reference in its entirety. The methods of the present invention are also suitable for acylation of modified nucleic acids such as, for example, peptide nucleic acids. Also suitable for N-acylation according to the methods of the present invention are MMI (methylenemethylimino) dimers, described in Bhat, B. et al., *J. Org. Chem.* 1996, 61, 8186.

An N-acylated nucleoside or nucleotide formed according to the method of the present invention is suitably protected for use in further synthetic procedures. For example, a N-acylated nucleoside can be used in the synthesis of oligonucleotides. Furthermore, N-acylated ologonucleotides can be used in synthesizing higher molecular weight oligonucleotides.

Following completion of desired synthetic procedures utilizing the protected nucleoside or nucleotide, the N-acyl protecting group can be removed. Treatment of the protected nucleoside or nucleotide with ammonia at 55° C. overnight will remove the N-acyl protecting group.

As mentioned hereinabove, the methods of the present invention, and products thereof, are amenable to automation. For example, nucleotides or nucleosides which are N-acylated according to the method of the present invention can be incorporated into oligonucleotides using an automated nucleic acid synthesizer (e.g., 380B from Applied Biosystems, Inc. or Model 7500 or 8800 from Milligen/Biosearch).

EXAMPLES

The following examples are merely illustrative of the present invention and should not be considered limiting of the scope of the invention in any way. These examples and equivalents thereof will become more apparent to those skilled in the art in light of the present disclosure and the accompanying claims.

Example 1: Preparation of N-benzoyl Tetrazole

To a stirring suspension of 1H-tetrazole (7.0 g, 0.1 mol) and triethylamine (15 ml, 0.12 mol) in anhydrous THF (300 ml), in a bath maintained at 0° C., was added benzoyl chloride (99%, 12.8 ml, 0.11 mol) slowly over 30 min. When addition was complete, the mixture was stirred for an additional 45 min. A precipitate formed, identified as triethylammonium hydrochloride (using NMR spectroscopy), was removed by filtration through a pad of Celite 545. The solvent was removed under reduced pressure while the bath temperature was maintained below 30° C. A residual oil was obtained. Crystallization of the residual oil in hexanes yielded N-benzoyltetrazole as colorless crystals. The crystals were removed by filtration, washed with hexanes (2×15 ml) and dried under vacuum for approximately 15 hours at room temperature. Yield: 15 g, 86%; m.p. 56–58, C; $^1$H NMR, (CDCl$_3$) δ 9.43 (s, 1H), 8.26-8.22 (d, J=, 2H), 7.79-7.54 (m, 3H); $^{13}$C NMR, (CDCl$_3$) 162.9, 143.7, 136.3, 132.7, 129.7 and 129.5. HRMS: (FAB) for C$_8$H$_7$N$_4$O (MH$^+$) 175.0620, found 175.0627.

Example 2: General Procedure for N-benzoylation of Nucleosides. Preparation of N-6-benzoyl-3'O-TBDPS-2'-O-methyl-5'-Formaldoxime Adenosine

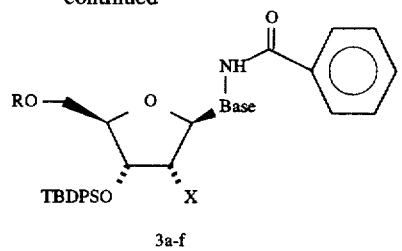

wherein R, "Base", and X are as indicated in Table 1.

TABLE 1

| CONDITIONS AND YIELDS OF ACYLATION OF NUCLEOSIDES | | | | | | |
|---|---|---|---|---|---|---|
| STARTING MATERIAL | PRODUCT | BASE | R | X | REACTION TIME (min.) | YIELD (%) |
| 1a | 3a | adenine | TBDPS | H | 75 | 80 |
| 1b | 3b | adenine | CH$_2$=N— | OCH$_3$ | 75 | 75 |
| 1c | 3c | adenine | DMT | H | 90 | 72 |
| 1d | 3d | 5-methyl cytosine | TBDPS | H | 15 | 80 |
| 1e | 3e | cytosine | DMT | H | 15 | 85 |
| 1f | 3f | 5-methyl cytosine | CH$_2$=N— | OCH$_3$ | 15 | 90 |
| 1g | 3g | 5-methyl cytosine | DMT | H | 15 | 80 |
| 1h | 3h | 5-methyl cytosine | DMT | O(CH$_2$)$_2$OCH$_3$ | 15 | 90 |

Crystalline N-benzoyl tetrazole (2 eq) was added to the nucleoside 3'-O-TBDPS-2'-O-methyl-5'-formaldoxime adenosine (1.14 g) and 4-dimethylaminopyridine (DMAP) in dry acetonitrile (5 mL/mmol) (1 equivalent nucleoside:2 equivalents N-benzoyl tetrazole:1 equivalent DMAP), and the mixture was stirred at 65° C. for 75 minutes. Yield was 75% of the monobenzoylated product only with no dibenzoylation observed. The solvent was removed uner reduced pressure and the residue was dissolved in ethyl acetate, washed with saturated aqueous NaHCO$_3$, and dried over anhydrous NaSO$_4$. The dried solution was filtered and concentrated to give a residue. The residue was purified by silica gel flash column chromatography using ethyl acetate-:hexanes:methanol (65/35/5, v/v/v) as the eluent to give 1.1 g (75%) of the title compound as a colorless foam. The compound was characterized by NMR spectroscopy and tlc comparison to the authentic sample.

Other nucleosides were benzoylated using the same procedure. Starting materials, products, base, reaction times and yields are shown in Table 1. The reaction can be represented as follows:

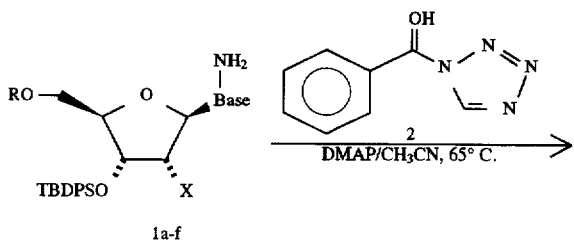

What is claimed is:

1. A method for selectively acylating an exocyclic amino group of a nucleoside or nucleotide, comprising reacting said nucleoside or nucleotide with N-acyl tetrazole.

2. The method of claim 1 wherein said N-acyl tetrazole is substantially pure.

3. The method of claim 1 wherein said N-acyl tetrazole is crystalline.

4. The method of claim 3, wherein said crystalline N-acyl tetrazole is dissolved in a sufficient quantity of a solvent to form a clear solution of said N-acyl tetrazole, and said solution is contacted with said nucleoside or nucleotide.

5. The method of claim 1 wherein said N-acyl tetrazole is N-benzoyltetrazole.

6. The method of claim 1 wherein said nucleoside is a purine nucleoside.

7. The method of claim 1 wherein said nucleotide is a purine nucleotide.

8. The method of claim 1 wherein said nucleoside is a pyrimidine nucleoside.

9. The method of claim 1 wherein said nucleotide is a pyrimidine nucleotide.

10. The method of claim 1 wherein said nucleoside is selected from the group consisting of deoxyadenosine, deoxycytidine, 2'-O-methyladenosine, 2'-O-methyl-5-methylcytidine, 2'-O-methoxyethylcytidine.

11. The method of claim 1 wherein said acylation is carried out in the presence of a base.

12. The method of claim 11 wherein said base is pyridine or a substituted pyridine.

13. The method of claim 1, wherein said acylation is carried out at a temperature of from about 50° C. to about 70° C.

14. The method of claim 1, wherein said acylation is carried out in a polar, aprotic solvent.

15. The method of claim 14 wherein said polar aprotic solvent is selected from the group consisting of acetonitrile, dimethylformamide, and DMSO.

16. A method for preparation of an N-acylated nucleotide or nucleoside, comprising reacting a nucleoside or nucleotide with an N-acyltetrazole.

17. The method of claim 16 wherein said N-acyltetrazole is N-benzoyltetrazole.

18. The method of claim 16 wherein said preparation is carried out using an automated synthesizer.

19. The method of claim 16, further comprising deacylation of said N-acylated nucleoside or nucleotide.

20. A substantially pure crystalline N-benzoyltetrazole.

\* \* \* \* \*